(12) United States Patent
Gross

(10) Patent No.: US 8,387,745 B2
(45) Date of Patent: *Mar. 5, 2013

(54) STETHOSCOPE COVER

(75) Inventor: John David Gross, Vista, CA (US)

(73) Assignee: Environmentally Smart Products, Inc., Vista, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/279,499

(22) Filed: Oct. 24, 2011

(65) Prior Publication Data

US 2012/0103718 A1 May 3, 2012

Related U.S. Application Data

(63) Continuation of application No. 12/409,930, filed on Mar. 24, 2009, now Pat. No. 8,042,646.

(60) Provisional application No. 61/039,332, filed on Mar. 25, 2008.

(51) Int. Cl.
*A61B 7/02* (2006.01)

(52) U.S. Cl. .......................... 181/131; 181/137

(58) Field of Classification Search .................. 181/131, 181/137; 600/528; 381/67
See application file for complete search history.

(56) References Cited

U.S. PATENT DOCUMENTS

| | | |
|---|---|---|
| 1,639,672 A | 8/1927 | Schraysshuen |
| 3,255,841 A | 6/1966 | Hasbrouck |
| 3,481,652 A | 12/1969 | Mazerolle |
| 4,248,241 A | 2/1981 | Tacchi |
| 4,701,169 A | 10/1987 | Steer |
| 4,765,321 A | 8/1988 | Mohri |
| 4,770,189 A | 9/1988 | Shyu |
| 4,777,961 A | 10/1988 | Saltzman |
| 4,850,023 A | 7/1989 | Yarush |
| 4,871,046 A | 10/1989 | Turner |
| 4,903,794 A | 2/1990 | Klippert et al. |
| 5,171,087 A | 12/1992 | Green |
| 5,349,961 A | 9/1994 | Stoddart et al. |
| 5,424,495 A | 6/1995 | Wurzburger |
| 5,448,025 A | 9/1995 | Stark et al. |
| 5,466,898 A | 11/1995 | Gilbert et al. |
| 5,497,426 A | 3/1996 | Jay |
| 5,528,004 A | 6/1996 | Wurzburger |
| 5,686,706 A | 11/1997 | Wurzburger |
| 5,747,751 A | 5/1998 | Weckerle et al. |
| 5,808,244 A | 9/1998 | Knight et al. |
| 5,920,038 A | 7/1999 | Foster |

(Continued)

FOREIGN PATENT DOCUMENTS

| | | |
|---|---|---|
| JP | 11-60418 | 3/1999 |
| WO | WO 2008/030461 A2 | 3/2008 |

OTHER PUBLICATIONS

PCT International Search Report and Written Opinion from PCT/US2009/038106 mailed May 15, 2009.

(Continued)

*Primary Examiner* — Jeremy Luks
(74) *Attorney, Agent, or Firm* — Knobbe Martens Olson & Bear LLP

(57) ABSTRACT

A cover for a stethoscope to prevent microbes from transferring from a patient to a stethoscope is disclosed. In one embodiment, a stethoscope cover comprises an antimicrobial barrier having a first and second surface, image forming material disposed on the antimicrobial barrier first surface, and an adhesive layer disposed on the second surface of the antimicrobial barrier to attach the antimicrobial barrier to a stethoscope. In some embodiments, the image forming material is configured to depict an image of a product. In some embodiments, the image forming material is configured to depict an image of an animal or character, to evoke feelings of happiness in a young patient.

20 Claims, 12 Drawing Sheets

U.S. PATENT DOCUMENTS

| | | | |
|---|---|---|---|
| 5,921,941 | A | 7/1999 | Longobardo et al. |
| 5,949,032 | A | 9/1999 | Wurzburger |
| 6,009,971 | A | 1/2000 | Weidman et al. |
| 6,019,186 | A | 2/2000 | Zambrano |
| 6,024,709 | A | 2/2000 | Stark et al. |
| 6,041,889 | A | 3/2000 | Stark et al. |
| 6,093,465 | A | 7/2000 | Gilchrist et al. |
| 6,179,783 | B1 | 1/2001 | Mohler |
| 6,206,134 | B1 | 3/2001 | Stark et al. |
| 6,289,616 | B1 | 9/2001 | Alvern |
| 6,324,289 | B2 | 11/2001 | Orten |
| 6,467,568 | B1 | 10/2002 | Kemper |
| 6,478,744 | B2 | 11/2002 | Mohler |
| D475,459 | S | 6/2003 | Wiles |
| 6,587,564 | B1 | 7/2003 | Cusson |
| 6,687,919 | B2 | 2/2004 | Dilworth, Jr. et al. |
| 6,848,204 | B1 | 2/2005 | Nowak |
| 6,971,504 | B2 | 12/2005 | Molinaro |
| 7,008,499 | B1 | 3/2006 | Wilson |
| 7,112,630 | B2 | 9/2006 | Lee et al. |
| 7,117,971 | B1 | 10/2006 | Cornacchia |
| 8,042,646 | B2 * | 10/2011 | Gross ............................. 181/131 |
| 2001/0045319 | A1 | 11/2001 | Kemper |
| 2002/0066219 | A1 | 6/2002 | Weidman |
| 2006/0248767 | A1 | 11/2006 | Hofer |
| 2007/0287960 | A1 | 12/2007 | Adams et al. |

OTHER PUBLICATIONS

SCOPESHIELD® Stethoscope Diaphragm Covers (online)—retrieved Feb. 22, 2010 from the Internet URL: http://www.safehomeproducts.com/shp2/product/scopeshield-reg-stethoscope-diaphragm-covers/stethoscope-accessories/257506/257506.aspx.

Disposable Stethoscope Covers (online)—Retrieved Feb. 22, 2010 from the Internet URL: http://www.hopkinsmedicalproducts.com/product.isp?path=11466&id=713.

* cited by examiner

STETHOSCOPE COVER

CROSS-REFERENCE TO RELATED APPLICATIONS

The present application is a continuation of U.S. patent application Ser. No. 12/409,930, filed Mar. 24, 2009 now U.S. Pat. No. 8,042,646, which claims the benefit of U.S. Provisional Patent Application Ser. No. 61/039,332, filed on Mar. 25, 2008. The disclosures of all the above-referenced applications, publications, and patents are considered part of the disclosure of this application, and are hereby incorporated by reference in their entirety.

BACKGROUND OF THE INVENTION

1. Field of the Invention

This application relates to a stethoscope cover that acts as a barrier to prevent the spread of microbes from patient-to-patient via a stethoscope. More particularly, this application relates to a stethoscope cover having image forming material disposed thereon.

2. Description of the Related Art

Patients expect doctors and hospitals to provide the most sterile environment possible for treatment. In some cases, however, patients become ill after a visit to the doctor due to the transfer of microbes from another patient. One way this can occur is through reuse of a stethoscope or other medical equipment that has not been properly cleaned or sterilized. The possibility of becoming ill during a routine check-up or contracting another illness during an appointment to treat a different ailment may diminish one's desire to seek treatment at the doctor's office. Some medical plans may fail to cover treatment for illnesses contracted from hospital and doctor's office visits, making it even more important for medical facilities to provide sterilized medical devices that are used on multiple patients, or provide a disposable alternative. Furthermore, medical facilities may be liable for health problems that they cause or fail to prevent. Accordingly, measures that help prevent the spread of diseases from patent-to-patient patients can benefit insurers, medical providers, and patients.

SUMMARY OF THE INVENTION

The system, method, and devices of the invention each have several aspects, no single one of which is solely responsible for its desirable attributes. Without limiting the scope of this invention, its more prominent features will now be discussed briefly. After considering this discussion, and particularly after reading the section entitled "Detailed Description of Certain Embodiments" one will understand how the features of this invention provide advantages over other stethoscope covers.

Stethoscopes are commonly used on multiple patients. Whether a stethoscope has been properly cleaned or sterilized is unknown to the patient. A "stethoscope cover" that covers a surface of a stethoscope that is normally placed in contact with a patient during an examination can be a barrier to prevent the transfer of microbes and infectious bacteria from a patent to a stethoscope, and then onto the doctor or another patient during a subsequent use of the stethoscope. Thus, the use of a stethoscope cover can remove the uncertainty of whether the stethoscope has been properly cleaned because it provides a barrier stopping microbes from a patient from ever contacting the stethoscope. The stethoscope cover may also provide additional benefits. In one embodiment, a stethoscope cover that includes an image which is visible to a patient can prevent the spread of microbes and provide a joyful distraction to a patient, especially a young patient.

The cover can be made from a paper or plastic material such that it can be supplied inexpensively as a disposable product. Embodiments of a stethoscope cover can include a base material, which can be flexible, relatively thin and generally fitted to the portion of the stethoscope that contacts a patient during its use, for example, the stethoscope diaphragm or bell. The base material is referred to herein as an antimicrobial barrier or layer. The cover can also include an image forming material disposed on a front surface of the antimicrobial barrier (the side of the cover disposed towards the patient when the cover is attached to a stethoscope) or the back surface of the antimicrobial barrier (the side of the cover attached to the stethoscope), or both. The image forming material can be ink, toner, dye, silver, pigment, or another substance capable of being configured to form an image.

An image (e.g., a picture, text, or symbol) formed by the image forming material may be disposed to cover an entire surface or a portion of a surface of the stethoscope cover. In one embodiment, the image can be one of a variety of cute, child-friendly images such that the stethoscope is perceived by a young patient as a non-threatening fun apparatus rather than an intimidating medical device. Thus, a stethoscope cover displaying an image may evoke feelings of joy and happiness, which can help the doctor-patient relationship. In another embodiment, the stethoscope cover may include an advertisement for a (medical) product or a company, thus increasing the patients exposure to product or company.

In one embodiment, a stethoscope cover comprises an antimicrobial barrier having a first surface and a second surface, image forming material disposed on the antimicrobial barrier first surface, and an adhesive layer disposed on the second surface of the antimicrobial barrier to attach the antimicrobial layer to a stethoscope. In one embodiment, the cover further comprises an antimicrobial substance. In one embodiment, the image forming material comprises the antimicrobial substance. In one embodiment, the image forming material comprises ink. In one embodiment, the cover further comprises a protective layer removably attached to the first side of the antimicrobial barrier. In one embodiment, the protective layer comprises image forming material. In one embodiment, the antimicrobial barrier comprises a first tab and the protective layer comprises a second tab. In one embodiment, the antimicrobial barrier and the protective layer are positioned such that the first and second tab are at least partially non-overlapping. In one embodiment, the antimicrobial barrier comprises at least one opening. In one embodiment, the adhesive layer is configured to cover a portion of the antimicrobial barrier. In one embodiment, the area of the antimicrobial barrier second surface is configured to be larger than a diaphragm of a stethoscope to which it attaches. In one embodiment, the antimicrobial barrier is not contoured to the shape of a stethoscope diaphragm. In one embodiment, the antimicrobial barrier comprises a removable portion and a series of perforations surrounding the removable portion. In one embodiment, the antimicrobial barrier, image forming material, and adhesive layer are sterilized.

In another embodiment, a stethoscope cover comprises means for shielding a portion of a stethoscope from contact with microbes, means for forming an image on the shielding means, and means for attaching the shielding means to a stethoscope. In one embodiment, the antimicrobial barrier means comprises a material comprising a first surface and a second surface. In one embodiment, the means for forming an image comprises image forming material. In one embodiment, the attaching means comprises an adhesive.

In another embodiment, a method of manufacturing a stethoscope cover comprises applying an adhesive on a first surface of an antimicrobial barrier, the antimicrobial barrier configured to cover at least a portion of a stethoscope bell or diaphragm, and placing image forming material on a second surface of an antimicrobial barrier, the image forming material configured to depict an image. In one embodiment, the method of manufacturing a stethoscope cover further comprises attaching a protective layer on the second surface of the antimicrobial barrier. In one embodiment, the method of manufacturing a stethoscope cover further comprises sterilizing the stethoscope cover.

In one embodiment, a cover for a stethoscope comprises an antimicrobial barrier comprising a first side and a second side, the first side comprising an image display region, an adhesive layer attached to the second side of the antimicrobial barrier, the adhesive layer configured for temporarily attaching the second side of the antimicrobial barrier to a surface of a stethoscope and image forming material disposed in the image display region.

In another embodiment, a cover for a stethoscope comprises means for forming an antimicrobial barrier comprising a first side and a second side, the first side comprising an image display region, means for attaching the second side of the antimicrobial barrier to a surface of a stethoscope, and means for forming an image in the image display region.

In one embodiment, a cover for a stethoscope comprises an antimicrobial barrier comprising a first side and a second side, the first side comprising an image display region, an adhesive layer attached to the second side of the antimicrobial barrier, the adhesive layer configured for temporarily attaching the second side of the antimicrobial barrier to a surface of a stethoscope so the image display region can be presented on a portion of the stethoscope viewable by a patient, and image forming material disposed in the image display region. The image forming material can comprise ink, toner, dye, pigment, silver, or another substance that can be used to form an image, and/or antimicrobial image forming material. The antimicrobial barrier can comprise a barrier material that prevents microbes from passing through said barrier. In some embodiments, the antimicrobial barrier is configured to cover a portion of a stethoscope diaphragm, for example, the entire surface of the stethoscope that contacts a patient during an exam.

The stethoscope cover can include an antimicrobial element. In some embodiments, the antimicrobial element comprises residual radiation, while in other embodiments there is not residual radiation even when a radioactive source is used to sterilize the cover and/or packaging. In some embodiments, an antimicrobial element can be disposed in a thin film barrier over the image forming material to form a protective antimicrobial surface that contacts a patient during operable use of the stethoscope. In some embodiments, the image forming material comprises antimicrobial ink. The protective barrier can include an image display region. The protective barrier can also include a tab extending beyond the antimicrobial barrier. The antimicrobial substance can include antimicrobial ink and/or an antimicrobial compound. In some embodiments, the cover can comprise a second antimicrobial barrier disposed on the image forming material. The circumference of the adhesive layer may be smaller than the circumference of the antimicrobial barrier. In some embodiments, the antimicrobial barrier comprises a first tab and the protective comprises a second tab, the first and second tabs being disposed such that the first tab and the second tab are at least partially not overlapping so as to allow easy access of either tab.

Another embodiment includes a method of manufacturing a stethoscope cover comprising providing a thin flexible material dimensioned to cover at least a portion of a stethoscope placed against a patient during operable use of the stethoscope, the material having a first side with an image display region and a second side with an adhesive layer disposed thereon, and placing an image on the image display region. In some embodiments the method can include attaching a protective foil barrier to the antimicrobial barrier such that the protective barrier covers the image display region of the antimicrobial barrier. In some embodiments, the protective foil barrier has an image display region. In some embodiments, the method can further include placing an image on the image display region of the protective foil barrier. In some embodiments the method can further include sterilizing the stethoscope cover, and/or packaging the stethoscope cover in a hermetically sealed container. The sterilizing may include exposing the stethoscope cover to radiation. For example, the cover can be irradiated by exposing it to a cobalt radiation source. Numerous covers can be irradiated at once.

Another embodiment includes a method of packaging the stethoscope cover described above, the method including attaching the adhesive side of the stethoscope cover to a bottom packaging barrier, and placing a top packaging barrier above the protective foil barrier of the stethoscope cover. In some embodiments, the packaging method is used for more than one stethoscope cover. In some embodiments, the top and bottom packaging barriers are perforated between each stethoscope cover.

Another embodiment includes a method of preventing the spread of microbes from a patient to a diaphragm of a stethoscope, the method comprising attaching a cover to the diaphragm, the cover comprising an image display region having an image contained therein.

DETAILED DESCRIPTION OF CERTAIN EMBODIMENTS

The following detailed description is directed to certain specific embodiments. However, the invention can be embodied in a multitude of different ways. Reference in this specification to "one embodiment" or "an embodiment" means that a particular feature, structure, or characteristic described in connection with the embodiment is included in at least one embodiment. The appearances of the phrase "in one embodiment," "according to one embodiment," or "in some embodiments" in various places in the specification are not necessarily all referring to the same embodiment, nor are separate or alternative embodiments mutually exclusive of other embodiments. Moreover, various features are described which may be exhibited by some embodiments and not by others. Similarly, one or more features may be described for one embodiment which can also be reasonably used in another embodiment.

Figure 1A:
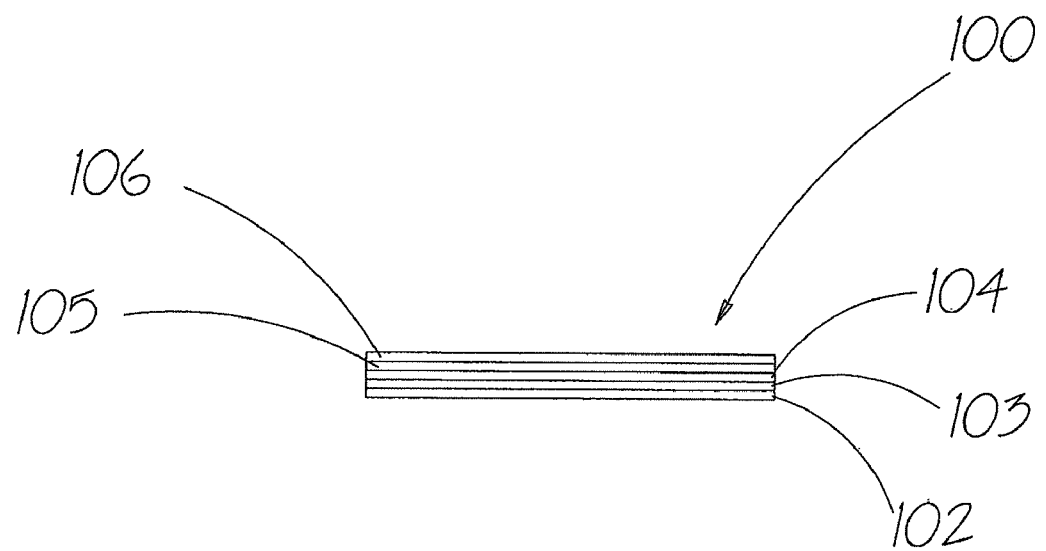
FIG. 1A illustrates an edge view of layers of a stethoscope cover, according to some embodiments.
Figure 1B:
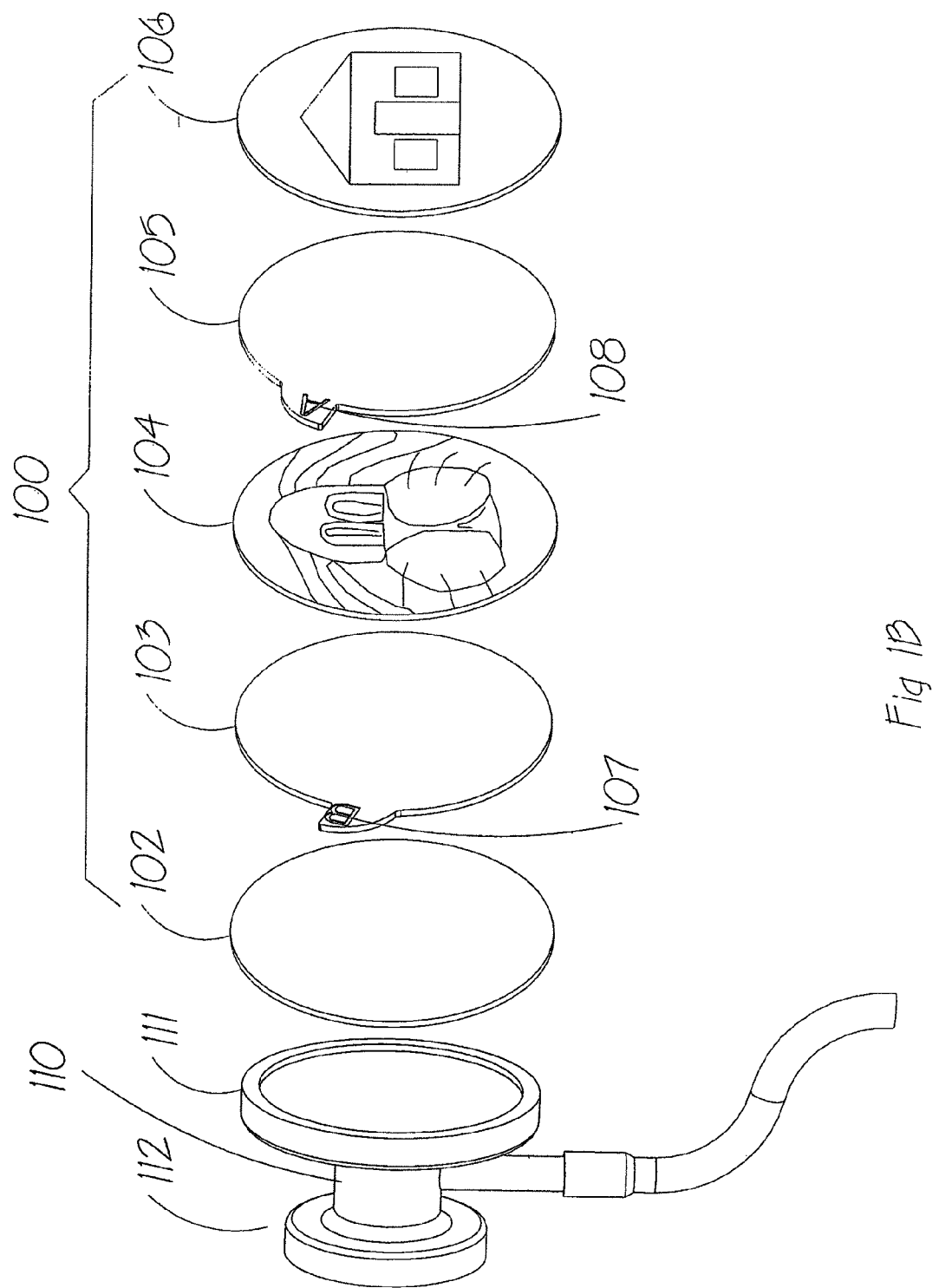
FIG. 1B illustrates an exploded view of the layers of the stethoscope cover illustrated in FIG. 1A.

FIGS. 1A and 1B illustrate embodiments of a stethoscope cover 100 that include one or more layers. FIG. 1A illustrates an edge view of such layers stacked together forming a cover 100. FIG. 1B illustrates a perspective separated view of the layers of the cover 100 which are illustrated in FIG. 1A. The stethoscope cover 100 includes an antimicrobial barrier 103, which is a physical antimicrobial shield between the stethoscope and the patient. In some embodiments, the antimicrobial barrier 103 is made from a flexible material. The cover 100 may precisely fit to the edges of the stethoscope face 111 to ensure no actual contact is made between the stethoscope and the patient. The cover 100 can be dimensioned to closely fit on the diaphragm 111 of a stethoscope 110. In one embodiment, the cover 100 is dimensioned such that at least part of the cover 100 is larger than the stethoscope diaphragm to which it attaches, which can aid in applying and/or removing the cover. For example, the antimicrobial barrier 103 may include a tab "B" 107. Although the antimicrobial barrier 103 is shown as a single layer in FIGS. 1A and 1B, in some embodiments the antimicrobial layer 103 comprises two or more layers. In one embodiment, the antimicrobial layer 103 is made of an absorbent material that allows the physician to use the antimicrobial layer 103 to take a culture from the patient that can be subsequently tested for microbes.

The antimicrobial barrier 103 may be made of various materials. In some embodiments, the antimicrobial barrier 103 comprises paper. The paper may be, for example, 60# bright white, high strength, matte-coated white litho paper stock designated for quality printing and high speed converting. Its physical characteristics may include a thickness (or caliper) of 0.0039+/−10% in., brightness reflectance at 75° angle of 88%, gloss reflectance at 75° angle of 12%, opacity of 92, tear of 54 g, tensile of 32 lbs./in, and basis weight (25"×38"/500 sheets) of 60+/−10% lbs. In some embodiments, the antimicrobial barrier 103 comprises a plastic, for example, poly-ethylene chloride or poly-vinyl chloride.

In some embodiments, the antimicrobial barrier 103 includes one or more substances capable of neutralizing or destroying microbes. In some embodiments, the antimicrobial barrier 103 itself is made from or includes an antimicrobial substance. In one embodiment, the antimicrobial barrier 103 is coated with an antimicrobial substance. For example, the coating may be DuPont™ TraSys® 8700 or DuPont™ Zonyl® NFPaper Fluoro-Protectant or Wacker Polyviol 2700 supplemented with antimicrobial technology such as i) Ag-Ion from Aglon Technologies, or ii) Single Walled NanoTube with stabilized lysozyme invented at Auburn University Samuel Ginn College of Engineering. Such substances can be included in an image display layer 104, or be disposed in another layer covering the image display layer 104 (not shown).

The cover 100 can also include an adhesive 102 disposed on a back surface of the antimicrobial barrier 103 to attach the cover 100 to a stethoscope bell or diaphragm. The adhesive 102 may cover a portion of the back surface of the antimicrobial barrier 103, or it may cover the entire surface, depending on the particular embodiment. The adhesive 102 may be configured as a layer (an "adhesive layer") which covers a portion or all of the back surface of the antimicrobial barrier 103. In some embodiments, the cover 100 does not include an adhesive 102 to attach the cover to the stethoscope. Instead, a material used to make the antimicrobial barrier 103 can have a natural adhesion characteristic so that it can adhere to a surface of the stethoscope without needing an adhesive. In some embodiments, the configuration of the adhesive 102 can be a substantially continuous layer, or a patterned layer that does not cover the entire surface on which it is disposed. The adhesive 102 may have adhesion characteristics to hold the cover 100 to a stethoscope, but also allow for its easy removal from the stethoscope. In some embodiments, the adhesive 102 is made from a permanent, rubber-based adhesive. In one embodiment, the adhesive can be MACTac's 710VHP adhesive.

Still referring to FIGS. 1A and 1B, the cover 100 may also include image forming material 104 disposed on the antimicrobial layer 103. In some embodiments, the image forming material 104 is disposed in a layer referred to herein as an image display layer 104. The term "image display layer" 104 is used herein to refer to a layer of material comprising the image forming material, and it may comprise one or more other materials. The image display layer 104 can include additional non-image forming material, for example, a binder, a protective coating, or an antimicrobial substance. In some embodiments (not shown), image forming material (e.g., an image display layer) is disposed on both sides of the cover 100. The image display layer 104 can be a separate layer containing image forming material so that when the image display layer 104 is disposed on the antimicrobial barrier 103 an image is displayed thereon. In some embodiments, the antimicrobial barrier 103 can have an image display layer 104 disposed on both front and back surfaces (with an image depicted by each) so that when the cover 100 is removed from the stethoscope 110 another image is revealed on the back of the cover 100. In some embodiments, the image display layer 104 may be configured on at least a portion of the front surface, the back, or both surfaces of the antimicrobial barrier 103. In the example illustrated in FIG. 1B, the image farming material depicts a dog. The image forming material may comprise ink, toner, silver, or any other suitable material which can depict an image. The image forming material can be configured to depict a desired image across all or a part of a surface of the antimicrobial barrier 103.

The image display layer 104 can comprise image forming material configured to depict an "image" comprising one or more letters, characters, words, symbols, pictures or images. Such images can be used to communicate text or images to a patient. In some embodiments, the text may refer to products and companies for advertising purposes; images may depict products or company logos. In another embodiment, an image may be configured to depict a cute animal or character. An image may affect or influence the patient towards a more positive demeanor by distracting the patient during an examination. The image may evoke feelings of joy, happiness and laughter, especially for children. The image could also delight pet owners in the presence of an attending veterinarian using the stethoscope cover.

In one embodiment, the image display layer 104 comprises one or more antimicrobial image forming materials to further prevent the transfer of microbes. For example, the image forming material can comprise antimicrobial ink. In some embodiments, antimicrobial ink can be provided by InkTec, headquartered in Korea. In some embodiments, the ink can be ink described in U.S. Pat. No. 7,112,630, Lee, et al. (hereinafter "Lee") incorporated herein by reference in its entirety. Lee discloses:

"A water-soluble, antimicrobial active polymer and an ink composition are prepared by coupling an antimicrobial active compound to a branch of polyvinylalcohol. An excellent antimicrobial effect is provided without affecting the properties of the ink composition that includes the polymer. The polymer is added to the ink composition in an amount of 1 to 10 parts by weight based on 100 parts by weight of the ink composition. The ink composition provides extended storage stability due to no coagulation, effective antimicrobial effect even in a printed picture, and no irritation to human skin." (Lee, Abstract.) "The water-soluble, antimicrobial active polymer of the present invention is obtained by introducing a silane derivative with excellent antimicrobial activity into a branch of a polyvinylalcohol which is used as a wetting agent or a thickening agent in a water-soluble ink. Unlike a conventional antimicrobial agent which is separately added to an ink composition, the water-soluble, antimicrobial active polymer is added to an ink composition as a moiety of the polyvinylalcohol." (Lee, col. 3, lines 43-51.)

In another embodiment, the antimicrobial ink can be Colorcon's No-Tox® Printing Inks. No-Tox printing inks are employed for direct and indirect contact applications involving food, medical devices and associated packaging. This ink uses Ag-Ion licensed from Ag-Ion Technologies.

The protective layer 105 is a physical barrier that covers the examination surface of the stethoscope cover 100 (e.g., the portion of the cover 100 that touches the patient) until the cover 100 is needed for an examination. The protective layer 105 may be referred to as a "protective foil." In one embodiment, the protective layer 105 can be removed by pulling on tab "A" 108. The antimicrobial barrier 103 is connected to tab "B" 107. This allows the protective layer 105 to be removed without contact with the examination surface of the stethoscope cover. Once removed, the protective layer 105 may be used initially as a swab to collect possible examples of contamination on a patient's skin before contact with the antimicrobial barrier is made. The swab may be preserved as a part of the patient's record. The tab A 108 and tab B 107 may be configures as different shapes, such as triangular, square, or circular.

In some embodiments, the protective layer 105 can comprise clear polypropylene self-wound overlamination tapes. In some embodiments, the protective layer 105 may have a thickness of 0.8 mm, a coating weight of 0.25 mg, and an overall thickness of 1.05 mm. The protective layer 105 may include an adhesive made from emulsion acrylic, a peel adhesive of 12 oz/in, a tensile strength of 16 lbs/in, an elongation of 140%, an application temperature of 32-150° F., and an operating temperature of 32-200° F. In one embodiment, the protective layer 105 can be made from Achem Industry America's Clear Advantage tapes. In some embodiments, the protective layer 105 can comprise plastic, for example, polyethylene chloride or poly-vinyl chloride. In some embodiments, the protective layer 105 comprises paper and/or or a metallic material.

The cover 100 may include image forming material disposed on the protective layer 105 comprise image forming material configured to depict an "image" comprising one or more letters, characters, words, symbols, pictures or images. Such images can be used to communicate text or images to a patient. In some embodiments, the text may refer to products and companies for advertising purposes; images may depict products or company logos. In another embodiment, an image may be configured to depict a cute animal or character. In some embodiments, a second image display layer 106 may be disposed on all or part of the front or back of the protective layer 105. In some embodiments, the cover 100 further comprises a second image display layer 106 disposed on the protective layer 105. Other embodiments may include additional barriers, fewer barriers, or different barriers, as described herein. The protective layer 105 may be removably attached to the top of the image display layer 104. In some embodiments, a portion, or all of a surface, or both sides, of the protective layer 105 can have the image display layer 106 disposed thereon. In some embodiments, an image is placed on both the antimicrobial barrier 103 and the protective layer 105.

Figure 2:
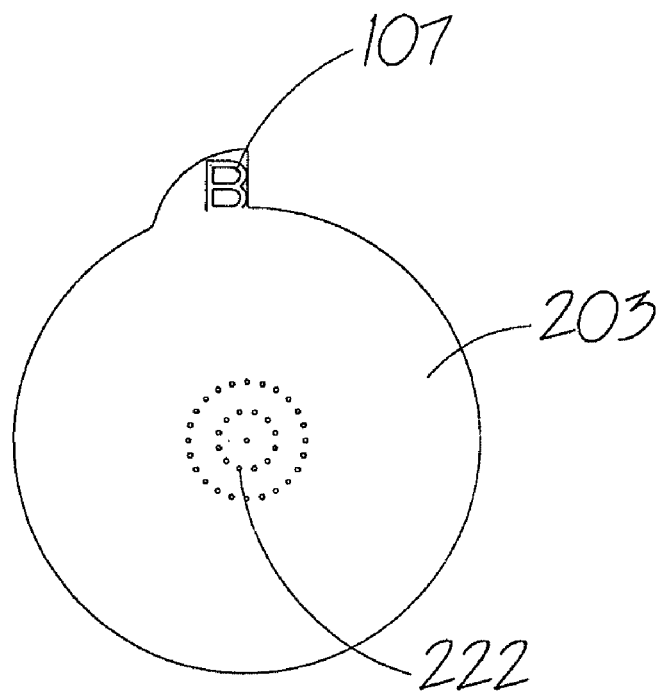
FIG. 2 illustrates an antimicrobial barrier of a cover having one or more openings.

FIG. 2 illustrates one embodiment of an antimicrobial barrier 203. In some embodiments, the antimicrobial barrier 203 includes one or more small openings 222, which may improve sound transmission through the antimicrobial barrier 103 so that the stethoscope cover does not interfere with sound quality during the examination. The openings 222 can be disposed across the surface of the antimicrobial barrier 203, or disposed in a certain portion of the surface, for example, the center or along the sides of an antimicrobial barrier 203. During use of a protected stethoscope, the cover is attached to the diaphragm or bell of the stethoscope. After the stethoscope has been used, the antimicrobial barrier 203 can be removed by pulling tab B 108 away from the stethoscope. This allows the stethoscope cover to be removed from the stethoscope without contaminating the examination surface of the stethoscope, or the surface of the cover that was against the patient.

Figure 3:
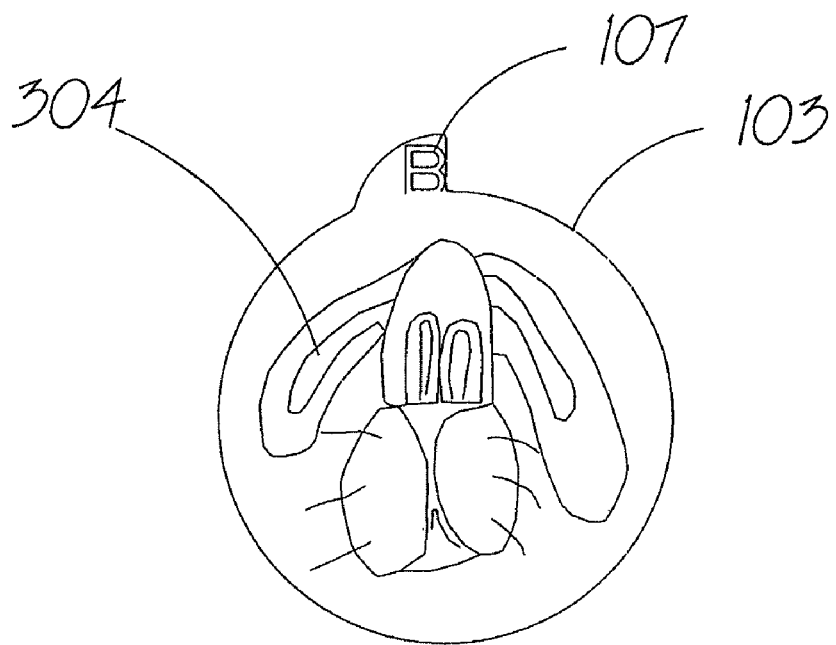
FIG. 3 illustrates the antimicrobial barrier having image forming material disposed on a antimicrobial barrier.

FIG. 3 illustrates one embodiment in which the antimicrobial barrier 103 has an image displayed thereon. FIG. 3 illustrates an antimicrobial barrier 103 with image forming material configured to depict an image of a dog 304, such as may be used by a physician working with children.

Figure 4:
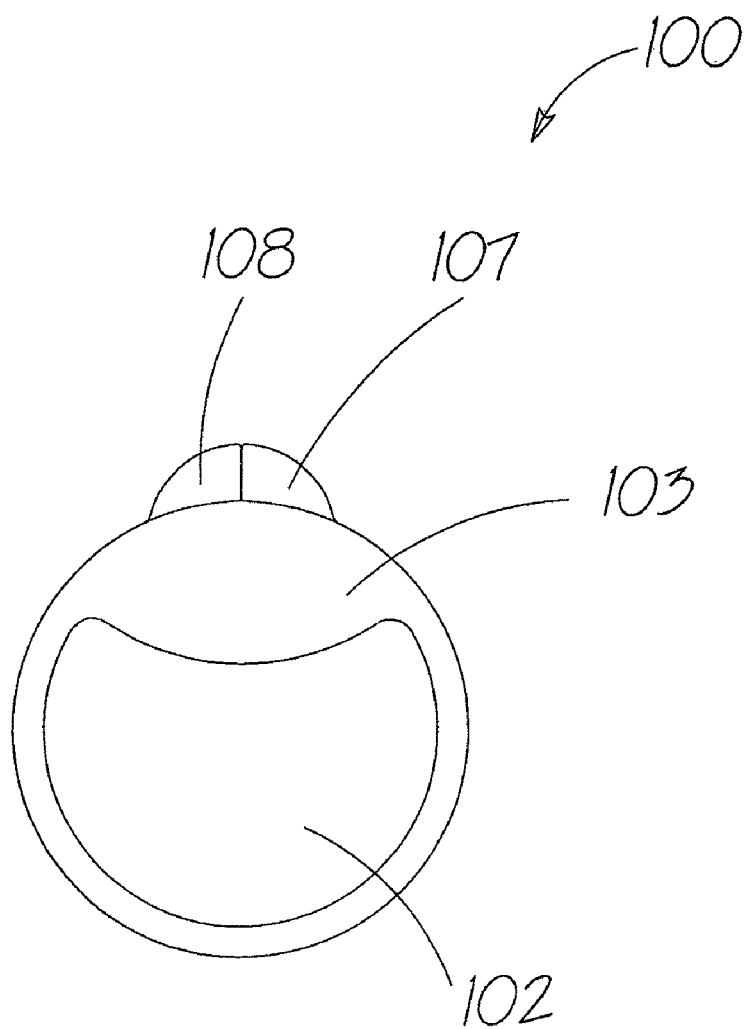
FIG. 4 illustrates a back view of a stethoscope cover according to one embodiment.

FIG. 4 illustrates another embodiment of a stethoscope cover 100, showing the (back) surface that attaches to the stethoscope. The adhesive 102 holds the antimicrobial barrier 103 to a portion of the stethoscope face 111. In one embodiment, the adhesive 102 does not extend to the outer edges of the antimicrobial barrier 103 cover in order to make the cover 100 easier to remove and less likely to contaminate the examination surface. This configuration, in combination with the tab A 108 and tab B 107 which are used for removing the protective layer 105 and the antimicrobial barrier 103 having an image formed on its front surface, provides a cover that is easy to remove and helps to make the appearance of the stethoscope friendlier and less threatening to children and perhaps animals.

Figure 5:
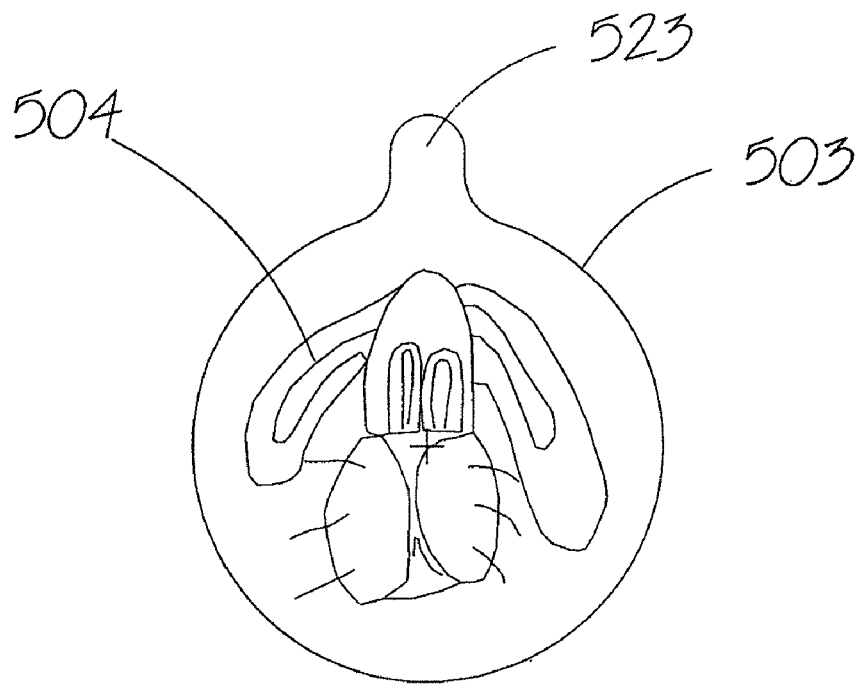
FIG. 5 illustrates another embodiment of an antimicrobial barrier of a stethoscope cover.

FIG. 5 illustrates an embodiment of a stethoscope cover with an antimicrobial barrier 503 having a single tab 523. Image forming material (here depicting a dog) is disposed on the antimicrobial barrier 503, for example, in an image display layer. In this embodiment, the protective layer 805 (not shown) is optional. The single tab is connected to the antimicrobial barrier 503. In another embodiment, the stethoscope cover does not include any tabs.

Figure 6:
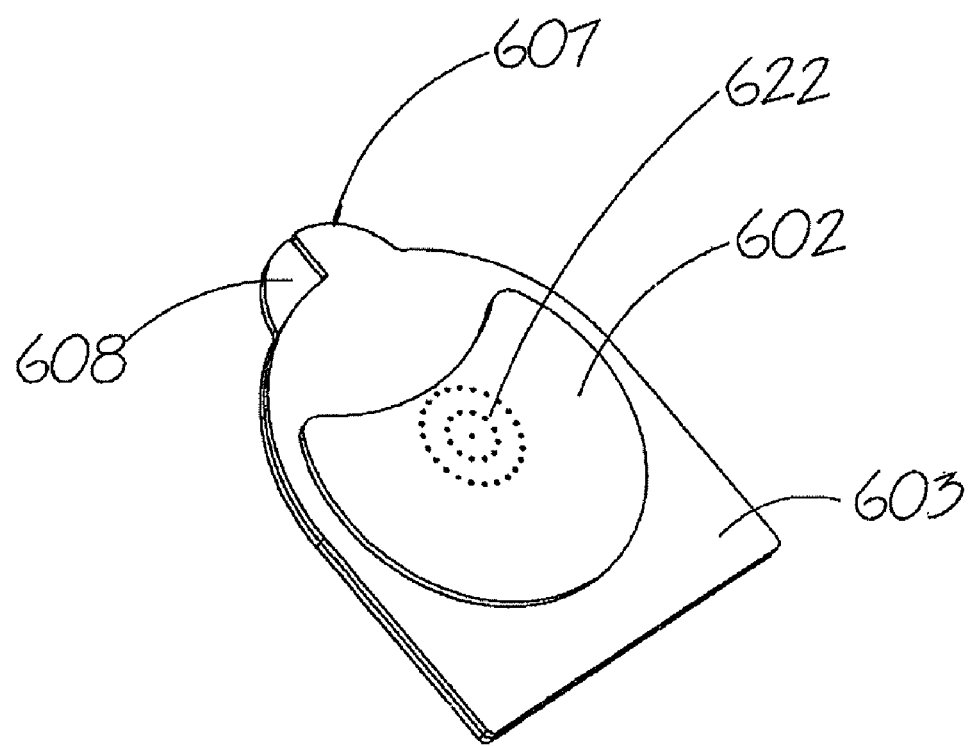
FIG. 6 illustrates a perspective view of another embodiment of a stethoscope cover.

FIG. 6 shows another embodiment of the stethoscope cover. In one embodiment, the stethoscope cover is only partially contoured to the stethoscope face 111 (FIG. 1B. For example, in FIG. 6, the stethoscope cover is contoured to the stethoscope face 111 at the top except for the tabs 607 and 608. However, the bottom edge is not contoured to the stethoscope face 111. For example, the bottom of the stethoscope cover can be straight as shown in FIG. 6. Such an embodiment allows the stethoscope cover to be more easily removed from the stethoscope face 111. In one embodiment, the stethoscope cover may be removed by pulling the bottom of the antimicrobial barrier 103 that is not contoured to the stethoscope face 101. In one embodiment, the stethoscope cover is not contoured to the stethoscope face 101, and the tabs 607 and 608 may not be needed. Additionally, the extra portion of the stethoscope cover not contoured to the stethoscope face 101 may be used to display an image or text such as a drug manufacturer's name. In one embodiment, the antimicrobial barrier 103 is larger than the stethoscope face 101. This allows the stethoscope cover to be more easily removed. Additionally, it is easier for a treating physician to place the larger antimicrobial barrier 103 so that it covers the entire stethoscope face 101.

Figure 7:
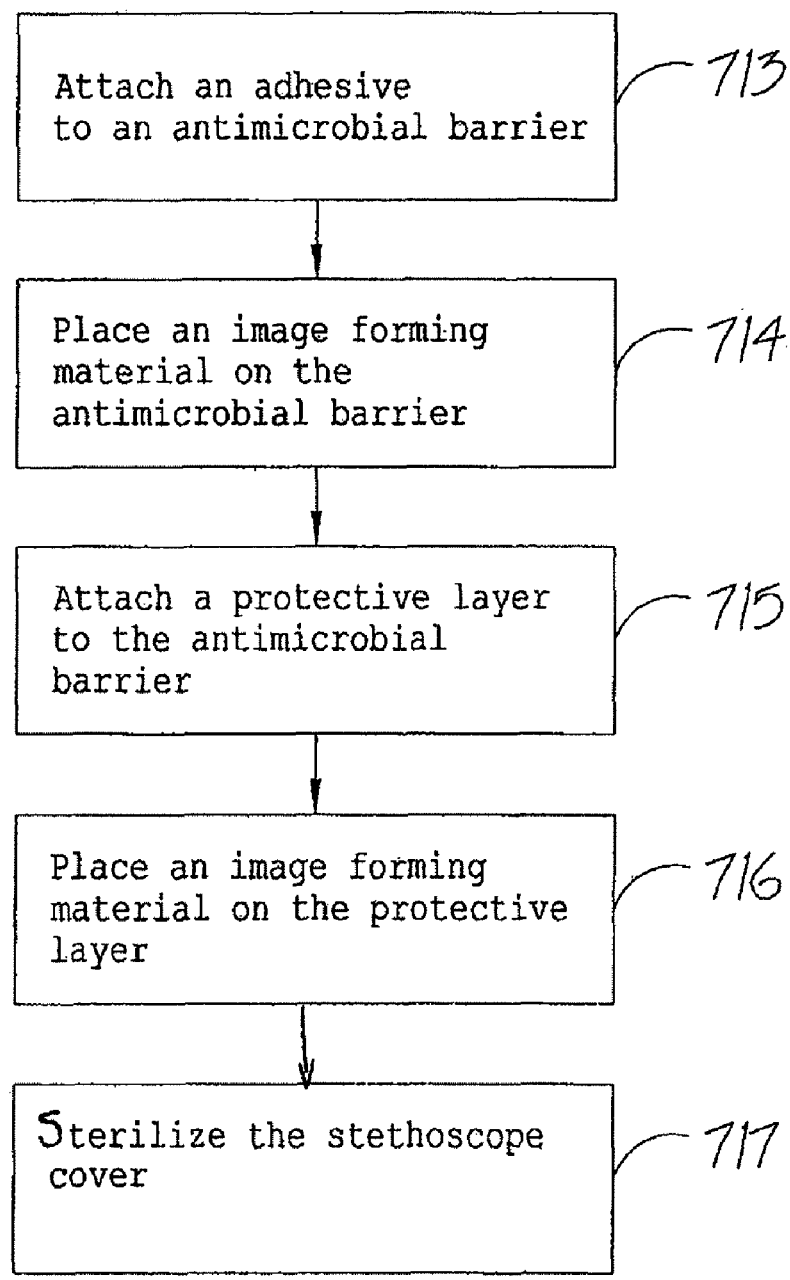
FIG. 7 is a flowchart illustrating the process for manufacturing a stethoscope cover.

FIG. 7 illustrates the process 725 of manufacturing a stethoscope cover. At 713, an adhesive 102 is attached to the antimicrobial barrier 103. Next at 714, an image forming material is placed on the antimicrobial barrier 103. At 715, the protective layer 105 is attached to the antimicrobial barrier 103. At step 716, an image forming material is placed on the protective layer 105. Finally, at step 717, the resulting stethoscope cover created at steps 713-716 is sterilized. In some embodiments, only steps 713 and 714 are used to make the stethoscope cover. Thus, steps 815, 816, and 817 could be left out of the manufacturing process. In another embodiment, only steps 713, 714, and 717 are used to make the stethoscope cover. In some embodiments, the protective layer 105 is placed on the antimicrobial barrier 103 as illustrated at step 715, but an image is not placed on the protective layer 105.

In one embodiment, the stethoscope cover can be dimensioned to fit the contours and/or dimensions of a stethoscope diaphragm. Although the covers herein are generally described as covering a stethoscope diaphragm, such covers can also be dimensioned and used to cover a stethoscope bell side. Accordingly, references herein to covering a diaphragm are understood as applicable to the bell of a stethoscope as well. Preferably, the cover is large enough to form a barrier between the stethoscope and the patient so that the stethoscope diaphragm does not contact the patient during while it is being used to examine the patient.

Figure 8A:
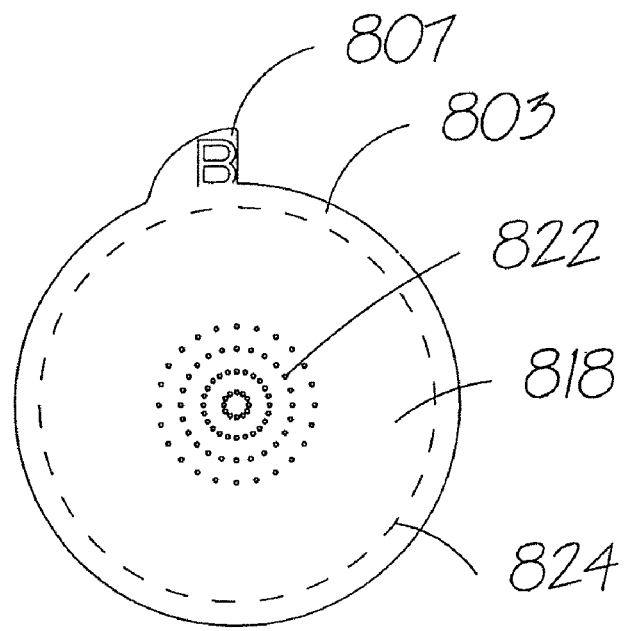
FIG. 8A illustrates a stethoscope cover that may be adjusted in size to fit a smaller stethoscope.
Figure 8B:
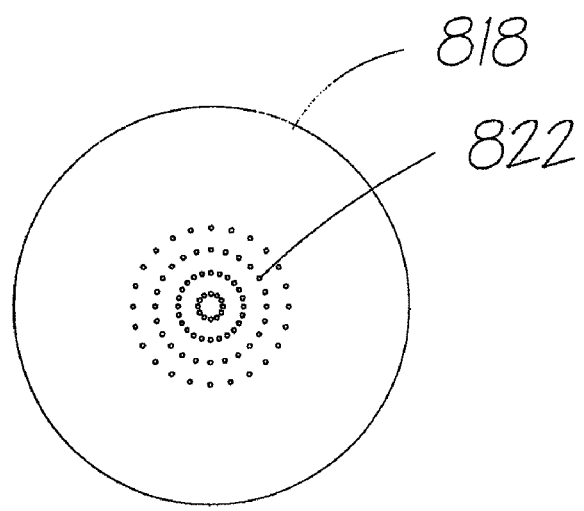
FIG. 8B illustrates a stethoscope cover that has been adjusted in size to fit a smaller stethoscope.

In some embodiments, the stethoscope cover is configured to fit over the edges of the stethoscope diaphragm, bell side and/or chest-piece. In some embodiments, a single stethoscope cover incorporates two sizes within one device in order to fit multiple sizes of stethoscopes or to fit either a diaphragm or a bell of a stethoscope. In one embodiment, the antimicrobial barrier 803 has a perforated inner circle 818 as illustrated in FIG. 8A. The perforated inner circle 818 is dimensioned to fit a smaller stethoscope diaphragm. In operation, the entire stethoscope cover including the antimicrobial barrier 803 can be applied to a small stethoscope. Once it is secured, outer ring of the antimicrobial barrier 803 can be removed along perforations 824 such that only inner cover 818 remains on the stethoscope. FIG. 8B illustrates the inner cover 818 with the outer ring removed (along perforations 824, FIG. 8*a*). In one embodiment (not shown), the inner perforated portion also includes a tab (e.g., similar to tab B 807) so that the smaller stethoscope cover can be easily removed. Since the anti-bacterial ingredients are applied to the entire contacting surface of the antimicrobial barrier 803, the remaining portion 818 may also contains these chemicals.

Figure 9:
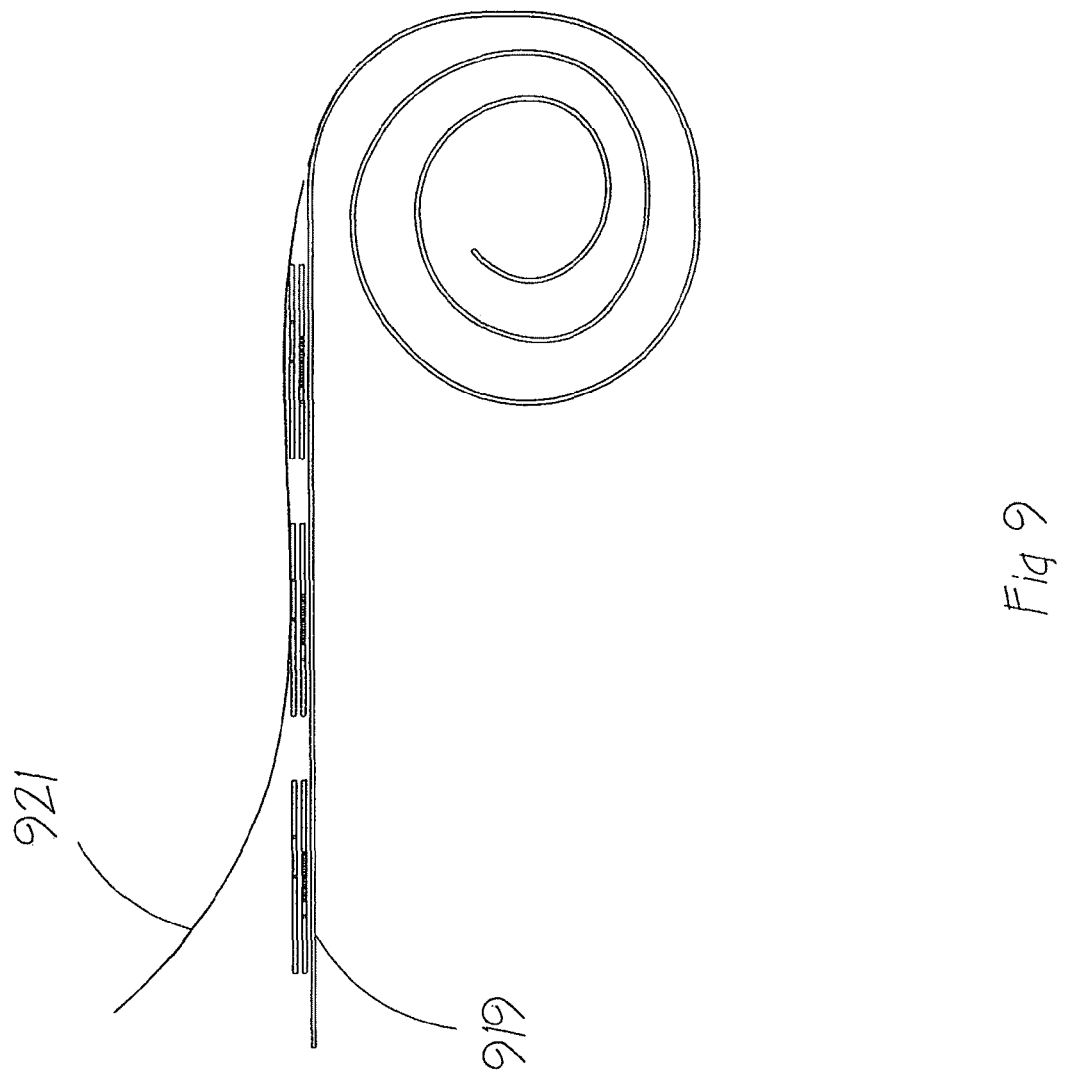
FIG. 9 illustrates packaging for a stethoscope cover, according to one embodiment.

Preferably, the stethoscope covers are packaged in a manner to keep them clean and sterile until they are used. In one embodiment, the stethoscope covers are packaged in a strip as illustrated by FIG. 9. This allows the stethoscope covers to be rolled and placed in a box or other container with an opening. In one embodiment, the packaging has two barriers. The bottom barrier 919 allows the adhesive layer 102 of the stethoscope cover to bond with it. In one embodiment, a light tack adhesive bonds barrier 919 to the stethoscope cover. The top barrier 921 forms a protective covering for the stethoscope cover. The top barrier 921 can be peeled back so that a stethoscope cover can be removed.

Figure 10:
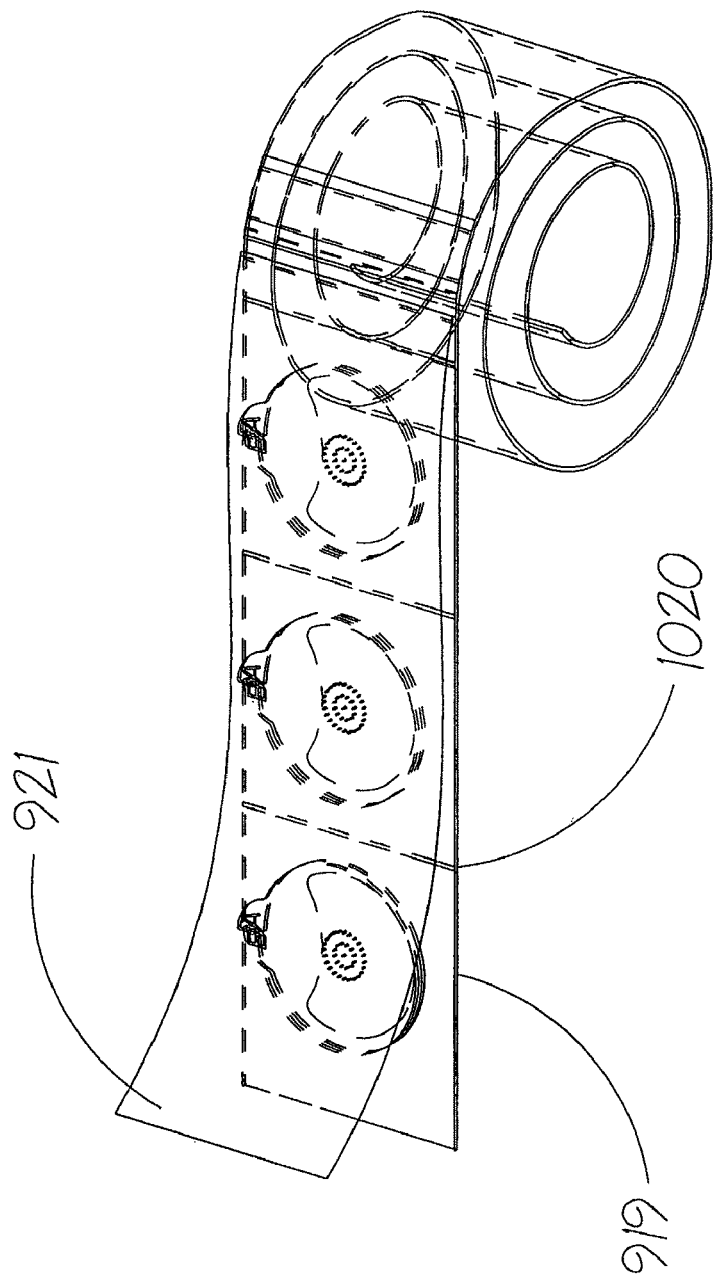
FIG. 10 illustrates packaging for stethoscope covers that are provided on a strip of material.

Referring now to FIG. 10, in some embodiments a stethoscope cover can be separated by a perforated edge 1020 in the two packaging barriers top barrier 921 and bottom barrier 919. This allows a physician to tear off one stethoscope cover at the time of examination. In one embodiment, the packaging is sealed at the perforated edges 1020 such that an individual stethoscope cover may remain sterile until the time of examination. In one embodiment, the perforation process as well as placing the stethoscope cover on the packaging strip is performed in one packaging step.

Figure 11:
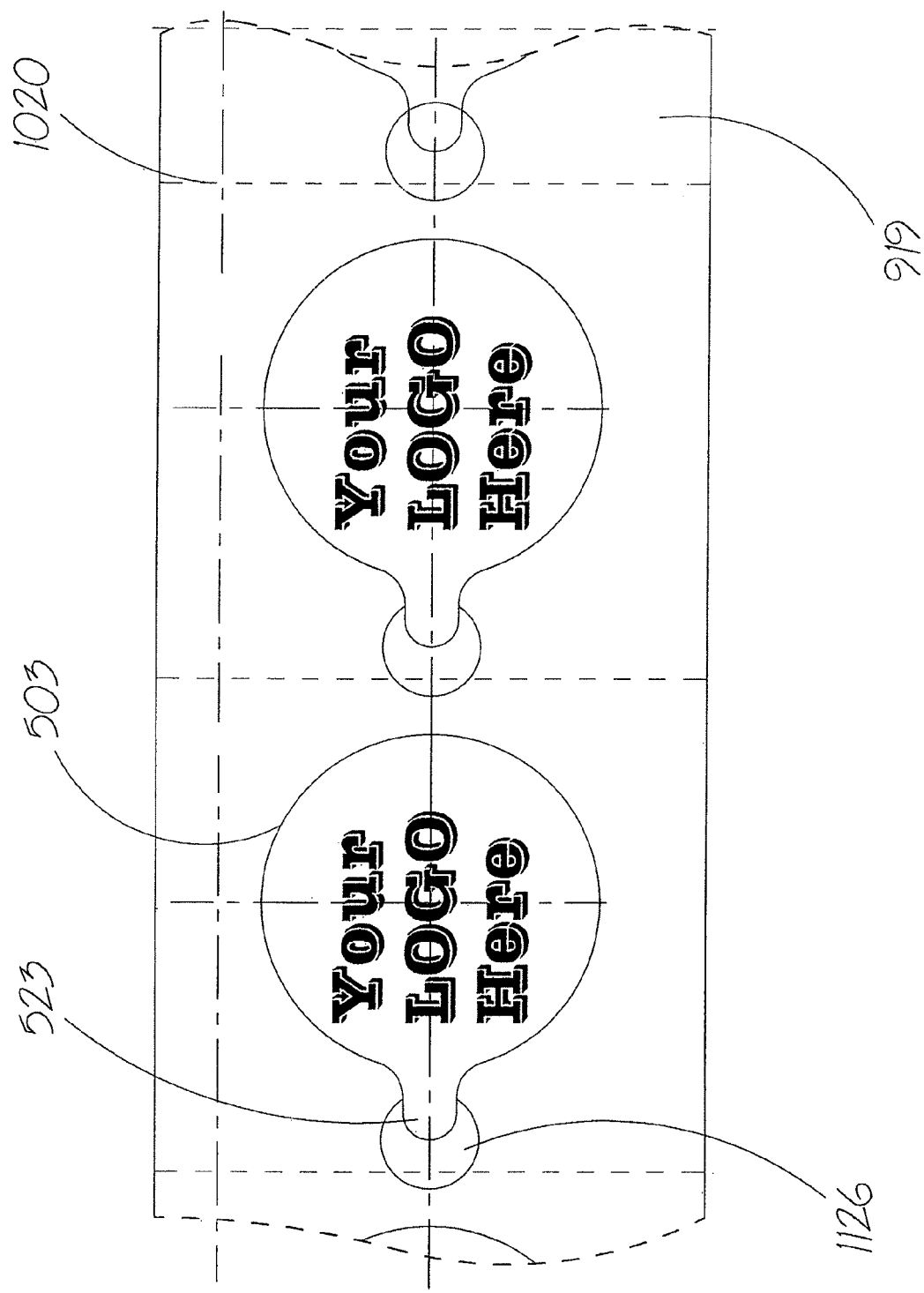
FIG. 11 illustrates another aspect of packaging for stethoscope cover.

Referring now to FIG. 11, in the packaging strip bottom barrier 919 there is a hole or indentation 1126 below tabs 523 in the single tab embodiment (or below tabs 107 and 108 in the double tab embodiment, such that a stethoscope cover could be easily removed from the packaging strip by pulling on tab 523. In one embodiment, the indentation 1126 is a half or full circle.

In one embodiment, the bottom packaging barrier 919 is made of a semi-bleached super-calendared kraft liner. The liner is coated with a release system designed specifically for label dispensing. In one embodiment the caliper is 0.0025+/−10% in. and the basis weight (24"×36"/500 sheets) is 40+/−10% lbs.

In one embodiment, the stethoscope is sterilized to eliminate any contaminants during the manufacturing process. In one embodiment radioactive cobalt is used to sterilize the stethoscope cover. It may be irradiated with Cobalt-60, which is commonly used for sterilizing medical equipment and consumer products, treating cancer patients, manufacturing plastics, and irradiating food. In one embodiment, the stethoscope cover is radiated with a dosage of between about 10 and 20 kilograys.

In one embodiment, companies such as Integra Biotechnical, LLC perform the sterilization using the Ontario Process Flow. First, the product is checked for the correct count, for damages, and for proper codes. The product is then received into the system and tagged. Next, counts, codes, and lot numbers are again verified against the customer's paperwork. Dosimeter placements are determined, and a run folder and necessary tags are created and set aside for a production run. Then, the product is stored together in a warehouse where it is labeled for production.

The product is then loaded for processing. At this stage, counts, disposition of the product, lot numbers, and product codes are again verified, and dosimeters are placed at the necessary position. To process the product through the machine, dosimeters are placed in compliance with the run folder positions, full totes of product with dosimeters and partial totes with dosimeters are sent into the irradiator for the scheduled laps or time, and the necessary dose is delivered to the product in regard to maximum and minimum customer set tolerances. The product is then unloaded from totes and stacked on pallets. Dosimeters are removed and accounted for, paperwork is completed, and the product is re-palletized and shrink wrapped.

The completed folder is then checked by a supervisor. The folder is reviewed, and dosimeters are read and verified to customer specifications. Finally, the sterilized product is released to the customer.

Various modifications to these examples may be readily apparent to those skilled in the art, and the principles defined herein may be applied to other examples without departing from the spirit or scope of the novel aspects described herein. Thus, the scope of the disclosure is not intended to be limited to the examples shown herein but is to be accorded the widest scope consistent with the principles and novel features disclosed herein. Accordingly, the novel aspects described herein is to be defined solely by the scope of the following claims.

What is claimed:

1. A disposable stethoscope cover, comprising:
a flexible base material having a first surface and a second surface;
an adhesive layer having a first surface and a second surface, the first surface of the adhesive layer disposed on the second surface of the base material to attach the base material to a diaphragm of a stethoscope;
an image display layer disposed on the first surface of the base material, the image display layer comprising image forming material;
an antimicrobial layer comprising an antimicrobial substance that can neutralize or destroy microbes disposed on the image display layer, wherein the image display layer is between the first surface of the base material and the antimicrobial substance, and wherein one side of the antimicrobial layer contacts the image display layer and the opposite side of the antimicrobial layer is exposed such that it contacts a patient during operable use of the stethoscope cover; and
a bottom barrier layer removably disposed on the second surface of the adhesive layer, the bottom barrier layer configured to be removed from the stethoscope cover prior to attaching the base material to the stethoscope diaphragm.

2. The cover of claim 1, wherein the image forming material comprises ink.

3. The cover of claim 1, further comprising a top barrier layer removably disposed on the opposite side of the antimicrobial layer such that the antimicrobial layer is between the top barrier layer and the base material, the top barrier layer configured to be removed from the stethoscope cover to expose the antimicrobial layer prior to contacting the patient during operable use of the cover.

4. The cover of claim 1, wherein the adhesive layer is configured to cover a portion of the second surface of the base material.

5. The cover of claim 1, wherein the area of the base material second surface is configured to be larger than a diaphragm of a stethoscope to which it attaches.

6. The cover of claim 1, wherein the base material, image forming material, and adhesive layer are sterilized.

7. An apparatus comprising a bottom strip including the bottom barrier layer of a plurality of stethoscope covers of claim 1, the second surface of the adhesive layer of each stethoscope cover disposed on the bottom strip.

8. The apparatus of claim 7, wherein the bottom strip comprises a perforated edge located between adjacent stethoscope covers.

9. The apparatus of claim 7, wherein each of the plurality of stethoscope covers of claim 1 further comprises a tab, and wherein the bottom strip comprises a hole below each tab of the plurality of stethoscope covers.

10. The apparatus of claim 7, wherein each of the plurality of stethoscope covers of claim 1 further comprises a top barrier layer removably disposed on the opposite side of the antimicrobial layer such that the antimicrobial layer is between the top barrier layer and the base material, and wherein the apparatus further comprises a top strip including the top barrier layer of the plurality of stethoscope covers, the top strip disposed over the opposite side of the antimicrobial layer of each stethoscope cover positioned on the bottom strip.

11. The apparatus of claim 10, wherein the bottom strip and the top strip are configured to be rolled with the plurality of stethoscope covers disposed between the bottom strip and the top strip.

12. The apparatus of claim 10, wherein the bottom strip and the top strip are sealed together at a perforated edge located between adjacent stethoscope covers.

13. A disposable stethoscope cover, comprising:
means for shielding a portion of a diaphragm of a stethoscope from direct contact when the stethoscope diaphragm is placed against an object, the shielding means having a first surface and a second surface;
means for attaching the shielding means to the stethoscope diaphragm, the attaching means having a first surface and a second surface, the first surface of the attaching means disposed on the second surface of the shielding means;
means for fanning an image on the shielding means, the image forming means disposed on the first surface of the shielding means;
means for destroying or neutralizing microbes, the microbes destroying and neutralizing means disposed in a layer covering the image forming means such that the image forming means is between the shielding means and the microbes destroying and neutralizing means, and wherein one side of the layer of microbes destroying and neutralizing means contacts the image for means and the opposite side of the layer of microbes destroying and neutralizing means is exposed such that it contacts a patient during operable use of the stethoscope cover; and
means for protecting the stethoscope cover, the protecting means removably disposed on the second surface of the attaching means, the protecting means configured to be removed from the stethoscope cover prior to attaching the shielding means to the stethoscope diaphragm.

14. The cover of claim 13, wherein the shielding means comprises a flexible material.

15. The cover of claim 13, wherein the means for forming an image comprises image forming material.

16. The cover of claim 13, wherein the attaching means comprises an adhesive.

17. The cover of claim 13, wherein the means for neutralizing or destroying microbes comprises an antimicrobial substance.

18. The cover of claim 17, wherein the antimicrobial substance is disposed in another layer covering the image forming means.

19. The cover of claim 13, wherein the protecting means comprises a strip coated with a release system.

20. The cover of claim 13, further comprising a top barrier layer removably disposed on the opposite side of the layer of microbes destroying and neutralizing means such that the layer of microbes destroying and neutralizing means is between the top barrier layer and the shielding means, the top barrier layer configured to be removed from the stethoscope cover to expose the layer of microbes destroying and neutralizing means prior to contacting the patient during operable use of the cover.

* * * * *

UNITED STATES PATENT AND TRADEMARK OFFICE
CERTIFICATE OF CORRECTION

PATENT NO. : 8,387,745 B2  
APPLICATION NO. : 13/279499  
DATED : March 5, 2013  
INVENTOR(S) : Gross Page 1 of 1

It is certified that error appears in the above-identified patent and that said Letters Patent is hereby corrected as shown below:

In column 2 (Title page 2 item 56) at line 15, under Other Publications, change
"path=11466&id=713." to --path=-1|466&id=713.--.

In the Specification:

In column 5 at line 60, change "Aglon" to --AgIon--.

In column 6 at line 45, change "farming" to --forming--.

In the Claims:

In column 12 at line 21 (approx.), in Claim 13, change "fanning" to --forming--.

In column 12 at line 30 (approx.), in Claim 13, change "image for means" to
--image forming means--.

Signed and Sealed this
Seventeenth Day of September, 2013

Teresa Stanek Rea
*Deputy Director of the United States Patent and Trademark Office*